(12) United States Patent
Sabet

(10) Patent No.: US 7,186,258 B2
(45) Date of Patent: Mar. 6, 2007

(54) LENTICULAR NET INSTRUMENTS

(76) Inventor: Sina J. Sabet, 5253 Winterview Dr., Alexandria, VA (US) 22312

( * ) Notice: Subject to any disclaimer, the term of this patent is extended or adjusted under 35 U.S.C. 154(b) by 602 days.

(21) Appl. No.: 10/322,346

(22) Filed: Dec. 18, 2002

(65) Prior Publication Data

US 2003/0135221 A1    Jul. 17, 2003

Related U.S. Application Data

(60) Provisional application No. 60/340,480, filed on Dec. 18, 2001.

(51) Int. Cl.
 *A61F 9/00*    (2006.01)
(52) U.S. Cl. ....................... 606/107; 606/127
(58) Field of Classification Search ................ 606/107, 606/166, 200, 113–114, 127, 161, 160; 604/122
See application file for complete search history.

(56) References Cited

U.S. PATENT DOCUMENTS

| | | | |
|---|---|---|---|
| 3,908,661 A * | 9/1975 | Kramer | ...................... 606/107 |
| 5,284,476 A * | 2/1994 | Koch | ........................ 604/274 |
| 5,676,669 A | 10/1997 | Colvard | |
| 5,707,359 A | 1/1998 | Bufalini | |
| 5,846,248 A | 12/1998 | Chu et al. | |
| 5,891,153 A * | 4/1999 | Peterson | ..................... 606/107 |
| 6,007,546 A | 12/1999 | Snow et al. | |
| 6,042,598 A | 3/2000 | Tsugita et al. | |
| 6,051,015 A | 4/2000 | Maahs | |

* cited by examiner

*Primary Examiner*—(Jackie) Tan-Uyen Ho
*Assistant Examiner*—Natalie Pous

(57) ABSTRACT

A lenticular net instrument comprises an elongate handle coupled with a lenticular net movable to contracted and expanded configurations via an actuator of the handle. The net in the contracted configuration has a narrow profile for insertion in and removal from a lens capsule through a small incision in the eye. The net is movable to the expanded configuration within the lens capsule behind a cataractous nucleus. The net has a plurality of openings therein of a size to prevent fragments of the cataractous nucleus produced by fragmentation with a fragmenting instrument from passing therethrough such that the fragments do not pass into the vitreous cavity. A method of cataract surgery involves deploying a net behind a cataractous nucleus upon the occurrence of a rupture in the capsular wall.

19 Claims, 5 Drawing Sheets

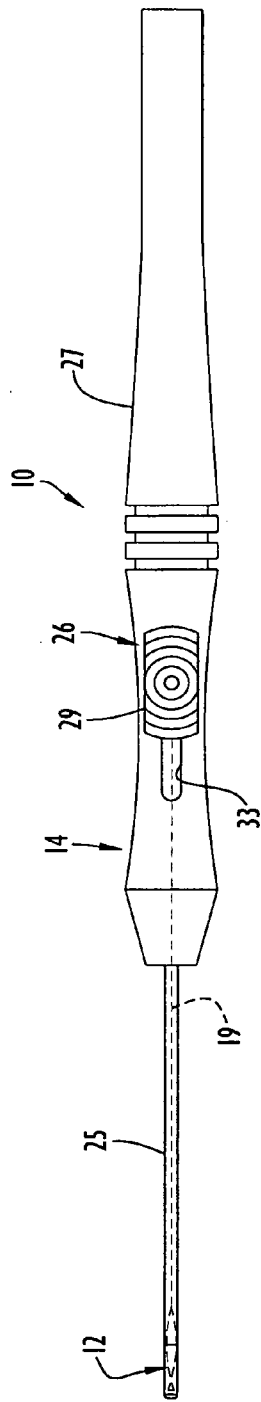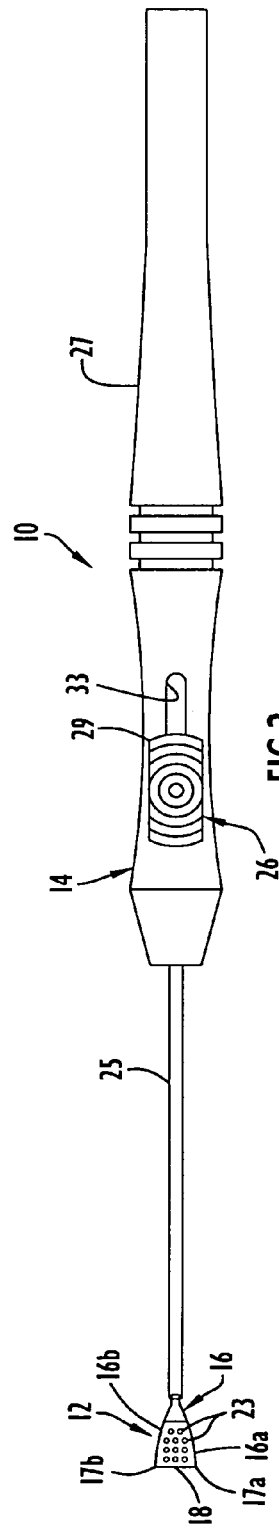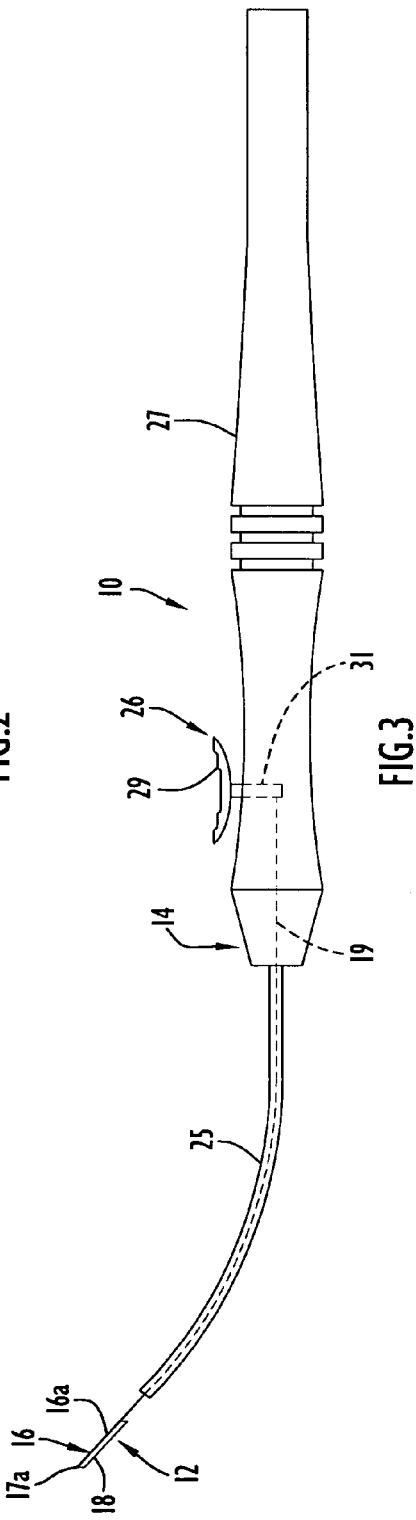

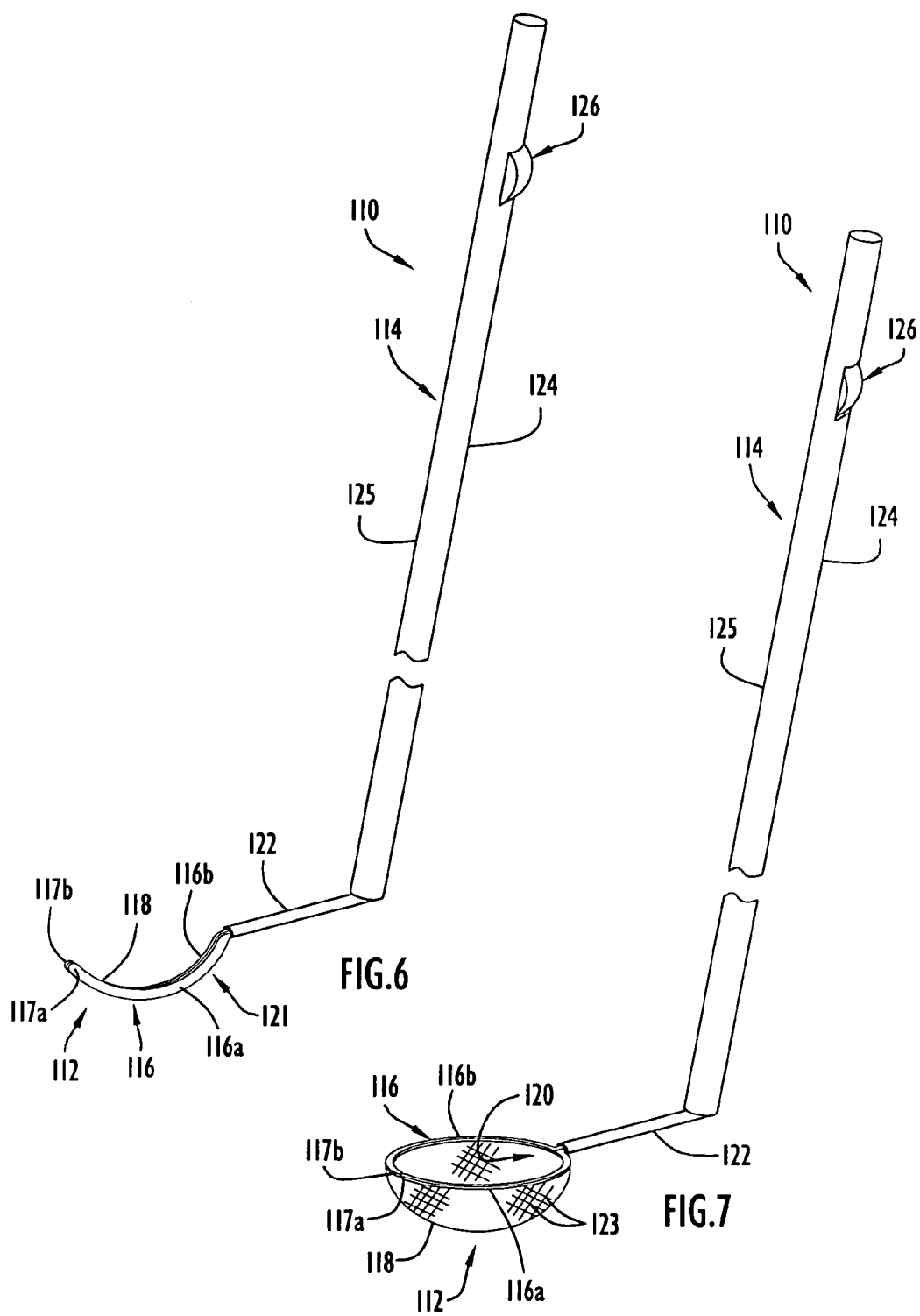

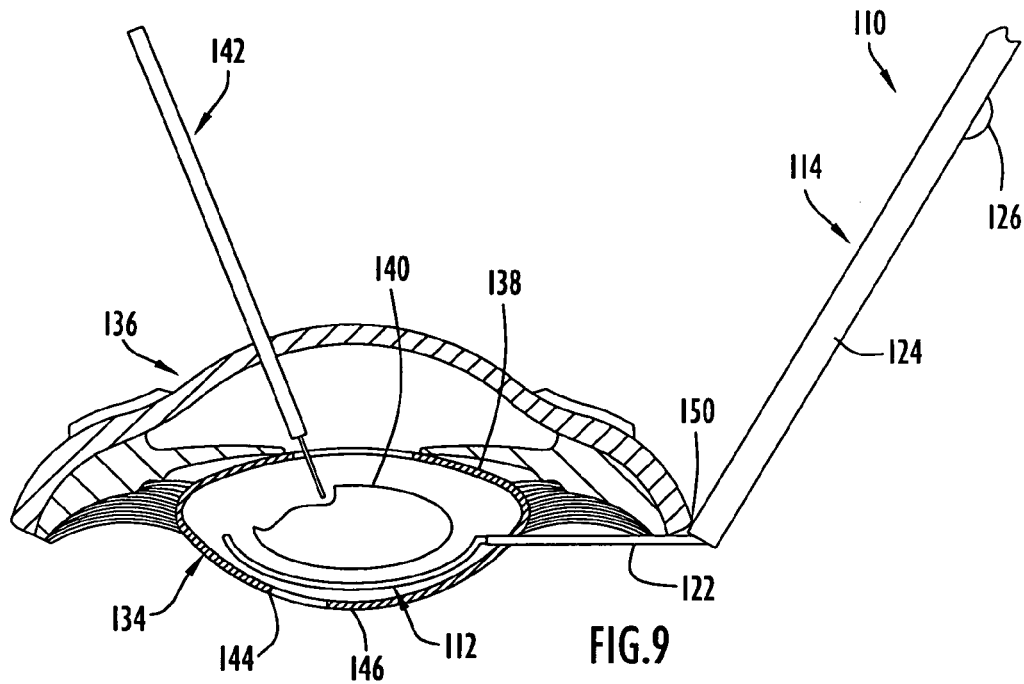
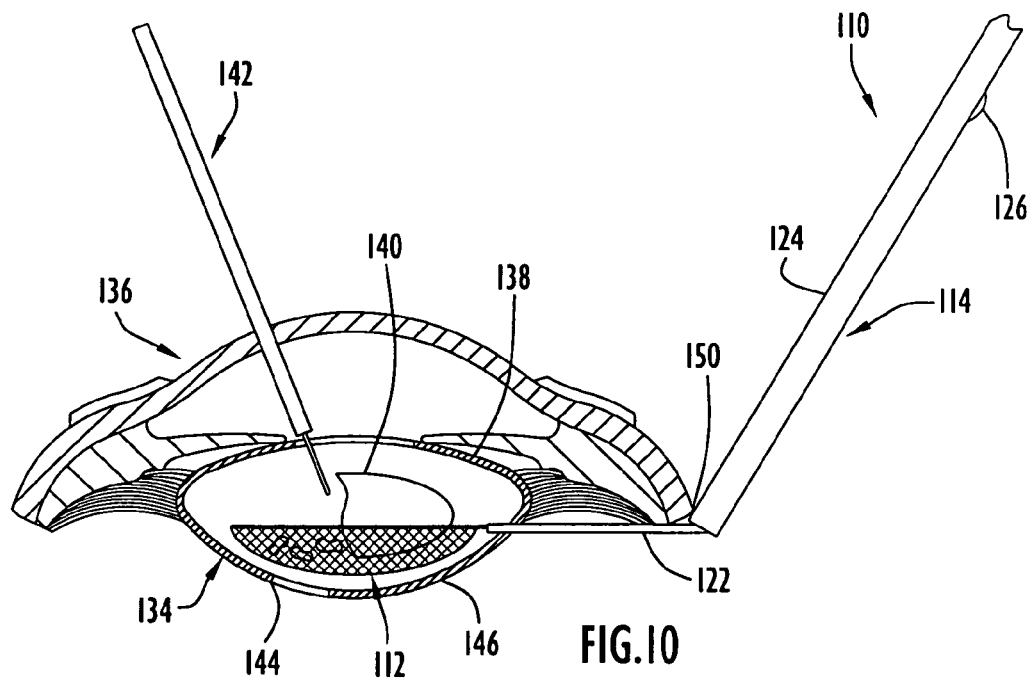

LENTICULAR NET INSTRUMENTS

CROSS-REFERENCE TO RELATED PATENT APPLICATION

The subject patent application claims priority from prior provisional patent application Ser. No. 60/340,480 filed Dec. 18, 2001, the entire disclosure of which is incorporated herein by reference.

BACKGROUND OF THE INVENTION

1. Field of the Invention

The present invention relates generally to ocular medical instruments and, more specifically, to safety net instruments for use in cataract surgery.

2. Discussion of the Related Art

During their lifetimes, many people become afflicted with cataracts, i.e. lenticular opacities that interfere with vision. Indeed, cataracts may be considered the most prevalent visually disabling eye disease in the world. The cloudiness or opacity associated with cataract arises in the nucleus of the anatomical lens, which includes a lens capsule also known as the capsular bag, the nucleus within the lens capsule, and gelatinous cortical material between the nucleus and the lens capsule. Currently, the only effective treatment for cataract is surgical removal of the cataract from the eye.

One method for surgical removal of a cataract is intracapsular cataract surgery or extraction, which involves removing the entire anatomical lens including the lens capsule. The lens capsule is removed essentially intact, with the cataractous nucleus contained therein. Intracapsular cataract surgery has numerous disadvantages including the need for undesirably large incisions to accommodate the lens capsule as it is withdrawn from the eye, prolonged recovery times, the risk that the vitreous body, normally contained behind the posterior capsular wall, may move forward into the anterior chamber of the eye, and potential complications including retinal detachment, cystoid macular edema, glaucoma, corneal decompensation and/or uveitis. Following intracapsular cataract surgery, vision is typically restored in the patient with corrective eye glasses or contact lenses, since the absence of the lens capsule makes it difficult for an intraocular lens implant to be properly supported in the eye.

Another method for surgical cataract removal is extracapsular cataract surgery or extraction. Extracapsular cataract surgery involves making an opening in the lens capsule and removing the nucleus and cortical material from the lens capsule, with the posterior capsular wall ideally remaining in place within the eye to inhibit movement of the vitreous body into the anterior chamber and to facilitate positioning of an intraocular lens implant. In extracapsular cataract surgery, the nucleus, which may be quite dense and hard particularly in the case of a mature cataract, is typically fragmented or broken up into smaller pieces, thereby allowing removal through a relatively small incision. The nucleus may be broken up or fragmented employing various fragmentation techniques and fragmenting instruments using, for example, mechanical, laser, electromagnetic or ultrasound energy. A preferred fragmentation technique is phacoemulsification, in which a fragmenting instrument delivers ultrasound energy to fragment or break up the nucleus, and the resulting nuclear fragments or pieces are typically removed from the eye by suction or aspiration through the fragmenting instrument.

Although extracapsular cataract surgery is usually preferred over intracapsular cataract surgery, extracapsular cataract surgery presents the risk that the posterior capsular wall may be ruptured inadvertently, such as due to unintended contact with the fragmenting instrument and/or due to the suction used to remove the nuclear fragments. Rupture of the posterior capsular wall during extracapsular cataract surgery gives rise to many of the same disadvantages associated with removal of the lens capsule in intracapsular cataract surgery. Particularly, mixing of nuclear material with the vitreous body may manifest as uveitis, resulting in an inflammatory reaction in the eye. A vitrectomy may be necessary to remove nuclear fragments or pieces from the vitreous body; however, a vitrectomy itself has potential adverse consequences, including retinal complications, for the patient. Complete removal of the nuclear material from the vitreous is difficult to accomplish; and, if all of the nuclear fragments or pieces are not removed, the patient is at risk for various complications including cystoid macular edema, glaucoma, corneal decompensation and uveitis. Often, removal of these fragments requires a secondary procedure by a retinal specialist, at considerable cost to the patient and/or third party payer.

It has been proposed to shield the lens capsule to protect against damage during surgical cataract extraction, but not to collect migrating nuclear fragments after the occurrence of a capsular rupture, as disclosed in U.S. Pat. No. 5,676,669 to Colvard. Colvard discloses a foldable, soft shield for being placed within the lens capsule between the nucleus and the posterior capsular wall prior to removing the nucleus during cataract surgery. The shield is placed in the lens capsule as a matter of course prior to fragmentation of the nucleus to protect the posterior capsular wall against possible damage. Since damage to the posterior capsular wall is not an inevitable occurrence during cataract surgery, the patient may be unnecessarily placed at increased risk from the shield being routinely inserted in the lens capsule. The shield, which is solid, has elastic memory biasing it to an expanded configuration. A relatively large incision is required to insert the shield in the eye in the expanded configuration. The shield must be deformed and then positioned within a rigid insertion cylinder for insertion of the shield in the eye through a smaller incision. The shield is ejected entirely from an end of the insertion cylinder into the lens capsule such that the shield is free and unattached within the lens capsule. The surgeon thereafter has no control over the shield as it automatically assumes the expanded configuration upon ejection from the insertion cylinder. The insertion cylinder is longitudinally straight and cannot be positioned around the nucleus to afford better control over shield position behind the nucleus. Regardless of whether the shield is in the expanded configuration or the collapsed configuration during insertion in the eye, the shield must follow the contour of the relatively denser and harder nucleus to randomly arrive at a position between the nucleus and the posterior capsular wall. Accordingly, the shield must be inserted in the eye prior to removal of the cataractous nucleus, and is not suited for insertion in the eye where some of the nucleus has already been removed. In order to remove the shield from the eye, the shield must be grasped with an instrument and pulled either into a withdrawal cylinder or directly through the incision. Grasping the shield with an instrument is tedious and time consuming and may require numerous trial and error attempts. Since the shield is solid, undesired pressure imbalances or differentials in the eye may occur due to there being no air or fluid flow through the shield.

Baskets or nets have been proposed for enclosing a cataractous nucleus and removing it from the eye as represented by U.S. Pat. No. 5,891,153 to Peterson and U.S. Pat. No. 3,908,661 to Kramer. Peterson discloses a basket for enclosing a cataractous nucleus, which is crushed by retraction of the basket into a tubular member and advancement of an auger into the interior of the basket. The basket is not collapsible in order to assume a narrow profile. The basket can be placed around the nucleus only by virtue of the nucleus being previously prolapsed into the anterior chamber of the eye or positioned so that one pole of the nucleus is above the anterior capsular wall. The nucleus must be directed into the basket using separate instruments. Kramer discloses a net having a self-expanding frame that is movable from a collapsed condition to an expanded condition automatically upon extension of the frame from a sleeve. Kramer requires that the nucleus be freed into the anterior chamber of the eye in order to be positioned in the net. The net containing the captured nucleus is retracted into the sleeve for removal of the nucleus from the eye, the nucleus being crushed by the net and the sleeve as the net is retracted. A major portion of the nucleus is squeezed outwardly through openings in the net and undesirably fall as fragments into the eye. These fragments must thereafter be removed by another procedure.

The need exists for a lenticular net that is positioned, as needed, between the nucleus and a ruptured capsular wall which occurs or may occur during cataract surgery subsequent to initiating fragmentation and aspiration of the nucleus, that is mechanically constrained in a contracted or collapsed configuration for insertion in the lens capsule through a small incision, that is controllably guided during insertion via a handle while constrained in the contracted configuration, that is mechanically moved to and maintained in an expanded configuration behind the nucleus to prevent or block migrating nuclear fragments or pieces from passing through the ruptured capsular wall while fragmentation and aspiration of the nucleus continue, that is mechanically returned to the contracted configuration for withdrawal from the eye subsequent to completion of fragmentation and aspiration, that remains attached to and controlled by the handle during insertion and withdrawal, and that permits flow therethrough while preventing the passage therethrough of migrating nuclear fragments.

SUMMARY OF THE INVENTION

Accordingly, it is a primary object of the present invention to overcome the aforementioned problems associated with capsular rupture during cataract surgery.

Another object of the present invention is to prevent nuclear fragments from migrating into the vitreous due to a capsular rupture during cataract surgery.

A further object of the present invention is to allow cataract surgery to safely continue in the event of capsular rupture.

An additional object of the present invention is to permit accurate, controlled placement of a lenticular net behind the nucleus.

The present invention has as a further object to provide a lenticular net that permits flow therethrough while preventing the passage therethrough of nuclear fragments and minimizing traction on the vitreous gel produced by fragmentation of the nucleus during cataract surgery.

It is also an object of the present invention to allow a lenticular net to be introduced in and withdrawn from a lens capsule through a small incision during cataract surgery.

Still another object of the present invention is to confine nuclear fragments in a lens capsule during cataract surgery to facilitate removal of the nuclear fragments via aspiration through a fragmenting instrument.

Moreover, it is an object of the present invention to deploy a lenticular net behind the lens nucleus only upon the occurrence of a ruptured capsular wall to prevent the migration of nuclear fragments through the ruptured wall during cataract surgery.

Some of the advantages of the present invention are that an additional instrument does not have to be introduced in the patient's eye unless needed; the extra cost associated with using an additional instrument unnecessarily is avoided; the lenticular net remains attached to the handle in the contracted and expanded configurations for enhanced control over proper guidance and positioning during insertion and removal from behind the lens nucleus; greater control over movement of the net to the contracted and expanded configurations is realized; the net preferably is, but does not have to be, retracted in and extended from a sleeve to effectuate movement between the contracted and expanded configurations; the sleeve is curved to facilitate deployment of the net between the nucleus and the posterior capsular wall; the cross-sectional size of the sleeve is small to permit insertion in and withdrawal from the eye through a small incision; the net is moved to the contracted configuration automatically by virtue of being withdrawn into the sleeve such that the net does not have to be deformed and then inserted in the sleeve; the interior or body of the net is not obstructed by structural components; the net does not rely on an intact nucleus for guidance to the proper position; the net does not have to be grasped with a separate tool for removal from the eye; the net may be conveniently introduced through a small incision without interfering with other instruments typically utilized during cataract surgery; cataract extraction procedures may safely be continued after capsular ruptures; the net is easily operable by surgeons of various skill and experience; and the lenticular net may be utilized in extracapsular cataract surgery using various techniques for fragmentation of the nucleus and is particularly contemplated for use in phacoemulsification.

These and other objects, advantages and benefits are realized with the present invention as generally characterized in a lenticular net instrument for use in extracapsular cataract surgery in which a fragmenting instrument is used to fragment a cataractous nucleus within a lens capsule. The lenticular net instrument comprises a lenticular net, a handle attached to the net and an actuator on the handle for selectively moving the net to a contracted configuration and to an expanded configuration. The net in the contracted configuration is mechanically constrained to assume a narrow, contracted profile permitting insertion of the net in a lens capsule through a relatively small incision in the eye and positioning of the net in the lens capsule at or adjacent a desired deployment site behind a cataractous nucleus which has started to sink behind a ruptured capsule into the vitreous cavity. The net is movable via the actuator from the contracted configuration to the expanded configuration in which the net has a predetermined expanded profile between the cataractous nucleus and the ruptured capsular wall. In the expanded configuration, the predetermined expanded profile of the net covers the rupture and may have a length and width to encompass the cataractous nucleus posteriorly. The predetermined expanded profile may correspond substantially to the anatomical curvature of the posterior capsular wall. The net in the expanded configuration between the cataractous nucleus and the ruptured capsular wall blocks or collects migrating fragments of the cataractous nucleus produced via fragmentation of the cataractous nucleus with a fragmenting instrument so that the fragments are prevented from falling further into the vitreous cavity while fragmentation of the nucleus continues during the cataract surgery. The net has a plurality of holes or openings therein of a size to prevent the passage therethrough of nuclear fragments while permitting flow therethrough to deter undue traction on the vitreous gel. Once fragmentation of the nucleus is completed and the nuclear fragments have been aspirated from the lens capsule, the net is moved from the expanded configuration back to the contracted configuration via the actuator for withdrawal from the eye through the small incision. The net may comprise a frame and a layer of openwork material attached to the frame, with the holes being provided in the openwork material.

In one embodiment, the frame comprises a pair of arms biased angularly outwardly away from one another in the distal direction in the expanded configuration, and the openwork material is attached to and extends between the arms. The net is extended beyond an open distal end of an elongate tubular sleeve of the handle in the expanded configuration, the actuator being used to effect extension of the net from the sleeve. As a result of being extended from the sleeve, the net automatically assumes the expanded configuration due to the bias of the arms. The net is retracted or withdrawn into the sleeve via the actuator to automatically move the net from the expanded configuration to the contracted configuration. The sleeve has a cross-sectional size permitting insertion in and withdrawal from the eye through the small incision. The openwork material is preferably a non-phacoemulsifiable material for use in cataract surgery where the fragmenting instrument is a phacoemulsifier.

The present invention is further generally characterized in a method of extracapsular cataract surgery comprising the steps of introducing a fragmenting instrument into a lens capsule containing a cataractous nucleus; fragmenting the cataractous nucleus with the fragmenting instrument; removing fragments of the cataractous nucleus from the lens capsule; introducing, in the event of a rupture in the posterior capsular wall, a lenticular net into the lens capsule through a small incision in the eye with the net in a contracted configuration assuming a narrow profile; moving the net from the contracted configuration to an expanded configuration between the nucleus and the ruptured posterior capsular wall; continuing fragmentation of the cataractous nucleus with the fragmenting instrument until the entire cataractous nucleus is fragmented; blocking migrating fragments of the cataractous nucleus with the net so that the migrating fragments do not pass through the rupture in the posterior capsular wall; and continuing removal of fragments of the cataractous nucleus from the lens capsule. Further steps include moving the net from the expanded configuration to the contracted configuration upon completion of fragmentation and aspiration and withdrawing the net from the eye. The step of introducing the net may include introducing the net through a pars plana incision or through a corneal limbus paracentesis incision. Preferably, the net is introduced through a 1 to 2 mm incision. The step of introducing a fragmenting instrument may include introducing a phacoemulsifier for fragmentation of the cataractous nucleus via ultrasound. The step of removing fragments and the step of continuing removal of fragments of the cataractous nucleus may include aspirating the fragments through the fragmenting instrument. The method may include retracting the net into a sleeve to obtain the contracted configuration and extending the net from the sleeve to obtain the expanded configuration.

Other objects and advantages of the present invention will become apparent from the following description of the preferred embodiments taken in conjunction with the accompanying drawings wherein like parts of each of the several figures are identified by the same reference characters.

BRIEF DESCRIPTION OF THE DRAWINGS

FIG. 1 is a top view of a lenticular net instrument according to the present invention in which a lenticular net thereof is in a contracted configuration retracted within a sleeve of a handle.

FIG. 2 is a top view of the lenticular net instrument depicting the lenticular net in an expanded configuration in which the net is extended from the sleeve.

FIG. 3 is a side view of the lenticular net instrument showing the lenticular net in the expanded configuration.

FIG. 6 is a broken perspective view of an alternative lenticular net instrument according to the present invention showing the lenticular net in the contracted configuration.

FIG. 7 is a broken perspective view of the alternative lenticular net instrument showing the lenticular net in the expanded configuration.

FIG. 9 is a broken view, partly in section, illustrating the alternative lenticular net instrument introduced in the eye through a pars plana incision with the lenticular net in the contracted configuration positioned between the nucleus and a ruptured posterior capsular wall.

FIG. 10 is a broken view, partly in section, showing the alternative lenticular net instrument with the lenticular net moved from the contracted configuration to the expanded configuration between the nucleus and the ruptured posterior capsular wall.

DETAILED DESCRIPTION OF THE PREFERRED EMBODIMENTS

Figure 4:
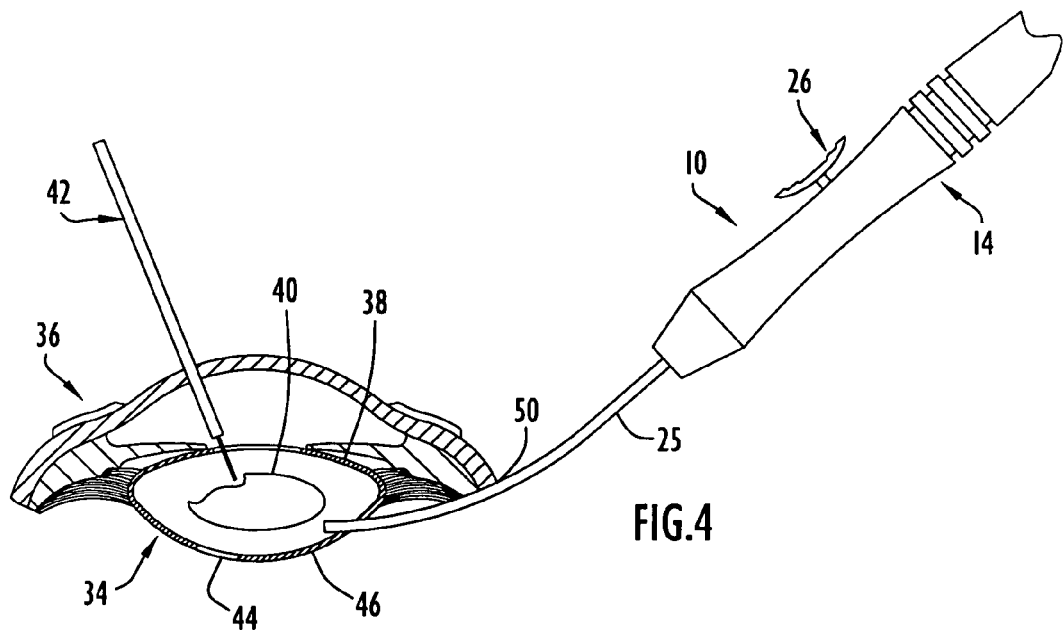
FIG. 4 is a broken view, partly in section, illustrating the lenticular net instrument introduced in the eye through a pars plana incision with the net in the contracted configuration.

A lenticular net instrument 10 according to the present invention is illustrated in FIGS. 1–3 and includes a lenticular net 12 attached to an elongate handle 14. The lenticular net 12 includes a frame 16 and a layer of openwork material 18 connected to frame 16. Frame 16 comprises first and second arms or frame parts 16a and 16b biased to extend angularly outwardly away from one another in opposite directions from a distal end of an elongate operating member 19 in an expanded configuration for net 12 as shown in FIGS. 2 and 3. In the case of lenticular net instrument 10, the central longitudinal axis of operating member 19 is disposed in a plane, and the arms 16a and 16b extend angularly outwardly on opposite sides of the plane in the expanded configuration. The arms 16a and 16b comprise wires of minimal cross-sectional size extending distally from the distal end of the operating member 19 to distal ends or tips 17a and 17b, respectively. In the expanded configuration for net 12, the arms 16a and 16b assume a generally V-shaped configuration as seen in FIG. 2. The arms 16a and 16b are made of biocompatible material such as a biocompatible metal having a spring force or bias capable of providing the necessary outward bias to maintain the expanded configuration. Preferably, the arms are capable of resiliently deflecting individually and in unison so as not to damage anatomical tissue which may inadvertently contact the arms when the net 12 is deployed in the expanded configuration in an anatomical lens capsule as explained further below. The distal end of operating member 19 is connected to proximal ends of the arms 16a and 16b, and the operating member includes a flexible or resilient shaft that may comprise one or more wires formed integrally, unitarily with the arms 16a and 16b or separately from the arms 16a and 16b. The operating member 19 is proximally coupled to an actuator 26 of the handle 14 and preferably has spring properties enabling it to resiliently flex or deform to follow the configuration of the handle when the operating member moves distally and proximally as explained further below. It is preferred that at least the portion of the operating member 19 that may be exposed in the eye be made of biocompatible materials including biocompatible metal spring materials.

The openwork material 18 spans the space defined between the arms 16a and 16b in the expanded configuration and has opposed lateral edges connected to the arms, respectively. The lateral edges of openwork material 18 extend lengthwise along the arms 16a and 16b and are continuously connected to the arms, respectively. The openwork material 18 has a distal edge extending transversely between the arms 16a and 16b at the distal tips 17a and 17b and has a proximal edge extending transversely between the arms a short distance distally of the distal end of operating member 19. The openwork material 18 is preferably a biocompatible plastic material and has a plurality of holes or openings 23 therein. The openwork material 18 can alternatively be a netting or mesh material made of plastic or other biocompatible materials including metals. Preferably, the openwork material 18 is made from a non-phacoemulsifiable material including non-phacoemulsifiable The openwork material 18 can be stretchable or non-stretchable to accommodate movement of the net 12 between the expanded configuration and a contracted or collapsed configuration described further below. The openwork material 18 can be designed to fold, pleat, crease or otherwise collapse when the net is moved from the expanded configuration to the contracted configuration and to unfold, open or expand when the net is moved from the contracted configuration to the expanded configuration, while being made of stretchable or non-stretchable materials. In the expanded configuration for net 12, the openwork material 18 may be slack or loose so as to define a receptacle having a mouth or entry opening between arms 16a and 16b, and the openwork material 18 may be curved or arcuate between arms 16a and 16b in the expanded configuration to accommodate and encompass the anatomical nucleus posteriorly. However, the nucleus remains uncaptured by the net 12 and is accessible for fragmentation by a fragmenting instrument separate and independent from the lenticular net instrument as explained further below. The curvature of the receptacle in the expanded configuration may correspond to the anatomical curvature of the posterior aspect of the lens as described further herein. The net has an expanded profile in the expanded configuration with a length and width sufficiently large to provide a barrier preventing migrating fragments or pieces of the nucleus produced during fragmentation from passing through the rupture in the posterior capsular wall. The holes or openings 23 in openwork material 18 are sufficiently small to prevent passage therethrough of significant migrating nuclear fragments while still permitting fluid flow therethrough. The openings 23 are preferably sized to prevent passage therethrough of any fragments of sufficient size to be of clinical significance.

Handle 14 comprises a handgrip 27 and an elongate tubular shaft or sleeve 25 extending longitudinally, distally from a forward end of the handgrip 27. The sleeve 25 has a curved configuration from the forward end of handgrip 27 to an open distal end of sleeve 25. Preferably, the distal end of the sleeve has a blunt configuration. The operating member 19 is disposed within the sleeve 25 and a proximal end of the operating member is coupled with the actuator 26 on the handgrip 27. The operating member 19 is slidably disposed in the sleeve 25 for movement longitudinally, distally and proximally relative to the sleeve 25 as effected via longitudinal sliding movement of the actuator 26 relative to and along the handgrip 27. The actuator 26 is configured as a finger pad 29 disposed externally along the handgrip 27 and a pin 31 extending from the finger pad to be slidably disposed in a longitudinal slot 33 of the handgrip. The proximal end of operating member is coupled to the pin 31 such that the operating member and, therefore, the net 12 is moved correspondingly with the actuator 26 as the actuator is moved along the slot 33. The slot 33 has forward and rearward ends for engaging the pin 31 to serve as stops limiting distal and proximal movement of the actuator 26.

When the actuator 26 is moved longitudinally proximally in the slot 33 as far as possible, the pin 31 is in engagement with the rearward end of slot 33 as shown in FIG. 1. With the actuator 26 moved proximally in the slot 33 as far as possible, the operating member 19 is moved longitudinally proximally relative to and within the sleeve 25 such that the lenticular net 12 is in a retracted position. In the retracted position, the lenticular net 12 is retracted entirely within the sleeve 25, and retraction of the net into the sleeve 25 causes the net to be moved from the expanded configuration of FIGS. 2 and 3 to the contracted configuration depicted in FIG. 1. Particularly, as the net 12 is drawn proximally into the sleeve 25, the arms 16a and 16b deflect or move inwardly toward one another to close or minimize the space that exists between the arms when the net 12 is in the expanded configuration. The arms 16a and 16b are moved inwardly toward one another due to engagement of the arms with the distal end of sleeve 25 as the operating member 19 is moved longitudinally proximally. As the arms 16a and 16b are moved inwardly toward one another, the layer of openwork material 18 folds, creases, pleats, or otherwise collapses and is drawn into the sleeve 25. It should be appreciated that the layer of openwork material 18 can be designed to fold, crease, pleat or otherwise collapse in a random manner or in a predetermined manner. As shown in FIG. 1, the distal tips 17a and 17b of arms 16a and 16b overlap and cross over one another in the contracted configuration; however, the arms 16a and 16b can have any orientation within the sleeve 25 in the contracted configuration. The net 12 in the contracted configuration has a narrow profile and, since the net is retracted in the sleeve 25, the cross-sectional size of the sleeve dictates the profile of the distal end of the instrument when the net is in the retracted position. The cross-sectional size of the sleeve is sufficiently small for insertion in and withdrawal from the eye via a small incision, such as a 1 to 2 mm incision. It should be appreciated that the operating member 19 can be coupled with the actuator 26 in many various ways either directly or indirectly via additional components or parts to enable the actuator 26 to effect longitudinal movement of the operating member 19.

The lenticular net 12 is moved from the contracted configuration of FIG. 1 to the expanded configuration of FIGS. 2 and 3 by moving the actuator 26 longitudinally distally along the slot 33 to effect longitudinal distal movement of the operating member 19 and the lenticular net 12 at the distal end of the operating member. Movement of the actuator 26 distally as far as possible in slot 33 as shown in FIGS. 2 and 3 results in the net 12 being extended or exposed from the open distal end of the sleeve 25. Exposure or extension of the net 12 beyond the distal end of the sleeve 25 causes the arms 16a and 16b to automatically move angularly outwardly to obtain the expanded configuration for the net 12, which is also in an extended position exposed distally from the sleeve 25 as shown in FIGS. 2 and 3. The handgrip 27 can have any configuration conducive to being grasped in a hand of a surgeon with the thumb of the hand resting upon the finger pad 29 to effect movement of the actuator. The handgrip 27 and/or the finger pad 29 can have ridges or any other structure to facilitate grasping or finger contact.

Figure 5:
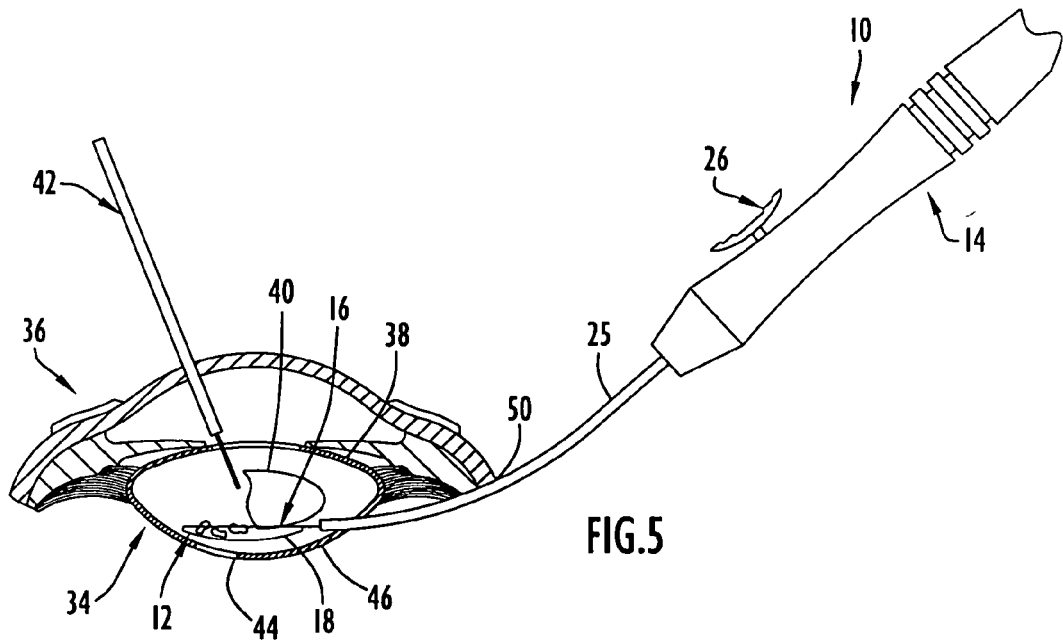
FIG. 5 is a broken view, partly in section, illustrating the lenticular net instrument with the net in the expanded configuration between the nucleus and a ruptured posterior capsular wall.

A method of extracapsular cataract extraction or surgery by lens phacoemulsification using the lenticular net instrument 10 is illustrated in FIGS. 4 and 5. FIG. 4 illustrates the anatomical lens 34 of eye 36, the lens 34 including lens capsule or capsular bag 38 containing a cataractous nucleus 40 and cortical material (not shown) between nucleus 40 and capsule 38. A fragmenting instrument 42 is introduced in the lens capsule 38, and the cataractous nucleus 40 is fragmented using the fragmenting instrument. Nuclear fragments produced as a result of fragmenting the nucleus 40 with the fragmenting instrument 42 are aspirated from the lens capsule, and the fragments may be aspirated through the fragmenting instrument 42. FIG. 4 shows the nucleus partially removed by fragmentation using the fragmenting instrument 42 and aspiration of the fragments of the nucleus from the eye through the instrument 42. The method of the present invention is particularly contemplated for use in phacoemulsification, in which case the instrument 42 is a phacoemulsifier. The lenticular net 12 is introduced in and deployed within the eye upon the occurrence of a rupture in the posterior capsular wall, and FIG. 4 illustrates a rupture, opening or hole 44 in the posterior capsular wall 46. Since the lenticular net 12 is not inserted in the eye until needed, the risk to the patient and the additional cost associated with introducing an additional instrument into the eye unnecessarily are avoided. If a rupture occurs in the posterior capsular wall 46, however, continuing the cataract extraction procedure in the presence of the rupture entails the risk that fragments of nucleus 40 may migrate and pass through the rupture into the vitreous body behind the posterior capsular wall. The typical cause of a rupture in the posterior capsular wall is damage from the fragmenting instrument or the suction applied for aspiration; and, accordingly, the lenticular net instrument 10 is deployed in the eye after fragmentation of the nucleus and aspiration of the fragments have been initiated.

Upon the occurrence of a rupture in the posterior capsular wall, the lenticular net 12 is introduced in the eye 36 and guided behind the lens fragments via manipulation of handle 14 and sleeve 25 as shown in FIG. 5. FIG. 4 shows the lenticular net instrument 10 introduced into the eye 36 through a small pars plana incision 50 about 1 to 2 mm in size with the net 12 in the contracted configuration retracted within sleeve 25, the cross-sectional size of sleeve 25 fitting within the incision 50. However, the lenticular net instrument may be designed for introduction in the eye through a small limbus paracentesis incision typically formed routinely in cataract surgery by many surgeons. Since the net 12 is retracted within the sleeve 25, no irregular surfaces or parts protrude from the sleeve 25 such that the distal end of the sleeve may be accurately and controllably guided via the handle 14 into a position behind the lens fragments. The curvature of the sleeve 25, which is rigid or substantially rigid, facilitates accurate and proper positioning of its distal end.

Once the distal end of sleeve 25 has been properly positioned behind the lens fragments, the actuator 26 is moved longitudinally, distally as far as possible along the slot 33 to extend the lenticular net 12 from the distal end of sleeve 25, causing the net to be automatically moved from the contracted or collapsed configuration to the expanded configuration behind the nucleus 40 as shown in FIG. 5. In the expanded configuration behind the nucleus 40, the net provides a physical barrier to the ruptured posterior capsular wall 46. The net may encompass the nucleus 40 posteriorly as shown in FIG. 5, but the nucleus remains uncaptured by the net for further fragmentation by the fragmenting instrument. With the net 12 so deployed, fragmentation of the nucleus with the fragmenting instrument 42 and aspiration of nuclear fragments produced thereby may safely resume or continue since migrating nuclear fragments are blocked by the net 12 from passing into the vitreous cavity. As described below for alternative lenticular net 112, the posterior nucleus may protrude into the receptacle defined by openwork material 18, and the net 12 may substantially follow or correspond to the curvature of the posterior aspect of the lens while leaving the nucleus uncaptured. Instead of passing through the rupture 44, migrating fragments of nucleus 40 will be blocked or collected by net 12, while flow of fluid is permitted through the net via the openings in openwork material 18 to minimize traction on the vitreous gel with movements of the instrument.

Once fragmentation and aspiration have been completed so that the cataractous nucleus 40 has been removed, the net 12 is retracted within the sleeve 25 for movement from the expanded configuration to the contracted configuration in a controlled manner such that any nuclear fragments which may be disposed on the net 12 will be captured and withdrawn into the sleeve 25 as the net is collapsed and retracted. The handle 14 is then manipulated to withdraw the sleeve 25 from the lens capsule 38 and from the eye 36 via the incision 50 with the net 12 in the contracted configuration retracted within the sleeve 25. Once the lenticular net instrument 10 is removed from the eye, an intraocular lens implant may be implanted in the eye to complete the cataract surgery.

An alternative lenticular net instrument 110 according to the present invention is illustrated in FIGS. 6 and 7 and includes lenticular net 112 attached to an elongate handle 114. The frame 116 for lenticular net 112 has a predetermined perimetrical or peripheral configuration defining or circumscribing an entry opening or mouth 120 in the expanded configuration for the net 112 as shown in FIG. 7. The frame 116 can have any desired predetermined perimetrical or peripheral geometric shape in the expanded configuration in accordance with the geometrical shape desired for an entry opening 120 of the receptacle defined by net 112 and, in the illustrated embodiment, the frame 116 is annular with a generally circular peripheral or perimetrical configuration as shown in FIG. 7. The frame 116 has a length and width, i.e. a diameter in the case of generally circular frame 116, in the expanded configuration. Preferably, the length and width of frame 116 in the expanded configuration are in the range of 5 to 6 mm to encompass the posterior of the nucleus of the anatomical lens when the net 112 is deployed in the expanded configuration between the nucleus and the posterior capsular wall. The net 12 may have length and width dimensions similar to those of net 112.

The frame 116 includes first and second frame parts or arms 116a and 116b, each having opposing ends. For the generally circular frame 116, each frame part 116a and 116b is a diametric or arcuate portion of frame 116 and has a generally semi-circular configuration. Each end of frame part 116a is pivotably or hingedly connected to a corresponding end of frame part 116b for movement of net 112 between the collapsed or contracted configuration shown in FIG. 6 and the expanded configuration shown in FIG. 7. The ends of frame parts 116a and 116b may be pivotably or hingedly connected in any suitable manner including the use of living hinges and mechanical hinges, and the pivots or hinges may be formed integrally, unitarily with the frame 116 or as separate components. Distal ends or tips 117a and 117b for frame parts 116a and 116b, respectively, are preferably rounded or radiused so as not to present any pointed edges or corners which could damage anatomical tissue within the eye.

Figure 8:
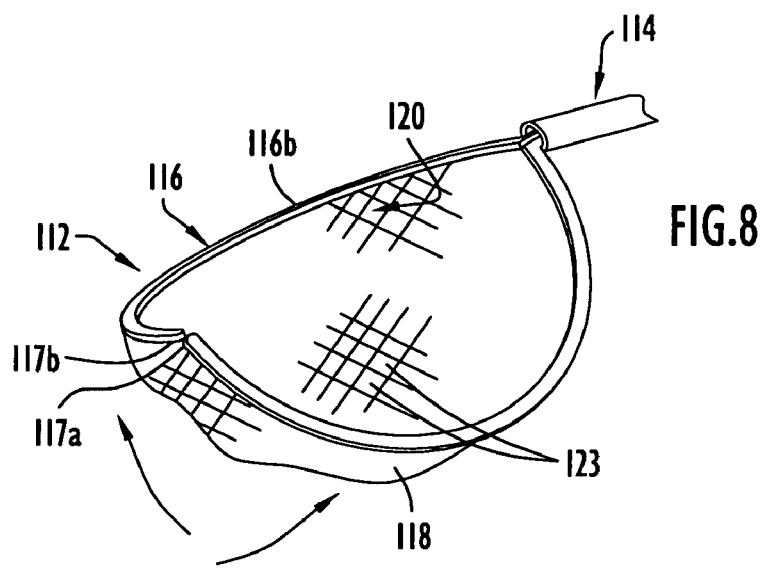
FIG. 8 is a broken perspective view of a distal portion of the alternative lenticular net instrument illustrating movement of the lenticular net from the contracted configuration toward the expanded configuration.

Frame parts 116a and 116b pivot or rotate about a diametric axis of rotation, coincident with the pivots or hinges at the ends of the frame parts, that extends diametrically across the entry opening 120 in the expanded configuration. The frame parts 116a and 6b pivot or rotate away from one another about the axis of rotation as shown in FIG. 8, for movement from the contracted configuration to the expanded configuration, with frame part 116a rotating in a direction opposite the direction of rotation for frame part 116b. Looking at FIG. 8, frame part 116a rotates in a clockwise direction about the axis of rotation, and frame part 116b rotates in a counterclockwise direction about the axis of rotation for movement from the contracted configuration to the expanded configuration. Conversely, frame parts 116a and 116b pivot or rotate toward one another about the axis of rotation for movement from the expanded configuration to the contracted configuration. Looking at FIG. 8, frame part 116a rotates in a counterclockwise direction about the axis of rotation, and frame part 116b rotates in a clockwise direction about the axis of rotation for movement from the expanded configuration back to the contracted configuration.

The frame 116 can have any desired cross-section, but is flat or planar in cross-section for the illustrated embodiment. Accordingly, the frame 116 has a flat or planar predetermined expanded profile disposed in the plane of entry opening 120 in the expanded configuration and, in the contracted configuration, has a flat or planar narrow contracted profile disposed in a plane perpendicular to the plane of entry opening 120 in the expanded configuration. The frame 116 is preferably of minimal width and height in cross-section so that the net 112 has a narrow, predetermined contracted profile in the contracted configuration. In particular, the cross-sectional width of net 112 in the contracted configuration is preferably 1 to 2 mm or less to permit insertion of the net in the eye through a 1 to 2 mm incision as discussed further below. In the contracted configuration, the frame parts 116a and 116b lie close and parallel to each other, and are in alignment with one another such that the net 112 forms an essentially singular, curved arm 121 having the predetermined contracted profile, which is of minimal and uniform width and height. Frame 116 can be flexible or rigid, but is preferably rigid or substantially rigid for enhanced control during insertion, as facilitated by the contracted profile for net 112. The distal ends 117a and 117b of frame parts 116a and 116b preferably cooperate to form a blunt or rounded distal end for arm 121. Other edges or corners of the frame parts 116a and 116b may be radiused or rounded to avoid trauma to intraocular tissue.

The openwork material 118 assumes a generally semi-spherical or partial-spherical configuration in the expanded configuration for net 112 so that the receptacle defined by net 112 in the expanded configuration also has a semi-spherical or partial-spherical configuration. The semi-spherical or partial-spherical configuration of the net 112 in the expanded configuration preferably corresponds to the curvature of the posterior aspect of the anatomical lens. In the illustrated embodiment, the semi-spherical or partial-spherical configuration assumed by net 112 in the expanded configuration is approximately a 30° arc. The openwork material 118, which may be rigid or flexible, collapses or contracts in the contracted configuration and is not substantially exposed from the frame 116 as shown in FIG. 6. In this manner, the narrowness and uniformity of the contracted profile are maintained, and the arm 121 does not present any significant protrusions or irregularities that would complicate insertion of the net 112 in the eye.

The openwork material 118 can be designed in various ways to collapse or contract in the contracted configuration for net 112. For example, the openwork material 118 can be designed to fold, crease, collapse or pleat, randomly or in a predetermined manner, when the net 112 is moved from the expanded configuration to the contracted configuration. The openwork material 118 is made of a non-phacoemulsifiable material, such as wire. The openwork material 118 has pores, interstices, holes or openings 123 which are sufficiently small to collect and prevent passage therethrough of fragments or pieces of the nucleus produced when the nucleus is fragmented or broken up during extracapsular cataract extraction while still permitting flow therethrough. The pores, interstices or openings 123 are preferably sized to collect and prevent passage therethrough of the smallest sized fragments or pieces expected to be produced by known fragmentation techniques and, in particular, by phacoemulsification.

Handle 114 for lenticular net instrument 110 can be angled, straight or curved depending on the location of the incision through which the net 112 is introduced in the eye. For introduction through a pars plana incision, the handle 114 is preferably angled as shown in FIGS. 6 and 7. Accordingly, handle 114 includes a handle shaft or sleeve 125 having a longitudinally straight distal portion 122 and a longitudinally straight proximal portion 124 disposed at an angle to distal portion 122. Distal portion 122 terminates distally at a distal end of handle 114 at which net 112 is disposed, and proximal portion 124 terminates proximally at a proximal end of handle 114. In the illustrated embodiment, proximal portion 124 defines an obtuse angle with distal portion 122; however, the proximal portion can be disposed at any desired angle to the distal portion conducive to ease of use. The distal portion 122 is in alignment with the axis of rotation and extends diametrically to the entry opening 120 in the expanded configuration so that the entry opening 120 faces perpendicularly to the distal portion. The distal and proximal portions 122 and 124 can have any desired cross-section. The distal portion 122 is typically inserted through the incision used to introduce the net 112 in the eye and, therefore, the cross-sectional size of distal portion 122 is preferably 1 to 2 mm or less to permit insertion through a 1 to 2 mm incision. The handle 114 may include a single elongate member or a plurality of elongate members. Handle 114 is shown as comprising concentric inner and outer tubular members, the inner member defining distal portion 122 and the outer member defining proximal portion 124. Depending on the manner in which the net 112 is moved between the expanded and contracted configurations, the inner and outer members may be fixed or non-movable relative to one another or may be rotatably and/or slidably movable relative to one another.

Handle 114 contains an operating member for mechanically moving net 112 between the contracted and expanded configurations. An actuator 126, such as a push button, a sliding knob, or any other actuator, is disposed on handle 114 to effect actuation or operation of the operating member. The operating member and actuator 126 can be designed in various ways and may include the various types of operating member and actuators typically found in surgical and medical instruments, such as intraocular scissors, for example, where a finger of the hand grasping the instrument is used to manually depress and release an actuator. Accordingly, the actuator 126, which includes a push button normally protruding from the handle 114 with the net 112 in the contracted configuration, is manually depressed to effect movement of the net 112 from the contracted configuration to the expanded configuration, and is released to effect movement of the net 112 from the expanded configuration back to the contracted configuration. It should be appreciated, however, that the actuator 126 can be designed to normally protrude from the handle with the net in the expanded configuration, to be depressed to effect movement of the net from the expanded configuration to the contracted configuration and to be released to effect movement of the net from the contracted configuration back to the expanded configuration. The operating member and actuator for lenticular net instrument 110 can be similar to the operating member and actuator for instrument 10.

The net 112 may be rendered geometrically or dimensionally stable in the contracted configuration due to the structure of frame 116 as well as being mechanically held in the contracted configuration by the operating member so long as the actuator 126 is not pushed in or depressed. The net 112 in the contracted configuration thusly maintains its predetermined contracted profile during insertion and positioning in the eye, and does not uncontrollably or randomly deform while being inserted and positioned in the eye. The frame 116 may be rendered geometrically or dimensionally stable in the expanded configuration due to the structure of frame 116 and the presence of a manual pushing force on actuator 126. The frame 116 in the expanded configuration for net 112 thusly maintains its predetermined expanded profile when deployed in the eye and does not uncontrollably or randomly deform when subjected to extraneous forces, such as contact with anatomical structures and/or other instruments. Of course, various locking mechanisms can be incorporated in or on the handle 114 for selectively locking the net 112 in the expanded and/or contracted configurations.

A method of extracapsular cataract extraction or surgery using the lenticular net 112 is illustrated in FIGS. 9 and 10 and is similar to the method described for instrument 10. FIG. 9 shows the lenticular net instrument 110 introduced into the eye 136 through a pars plana incision 150 about 1 to 2 mm in size. However, the lenticular instrument 110 may be designed for introduction in the eye through a small limbus paracentesis incision typically formed routinely in cataract surgery by many surgeons. The lenticular netinstrument 110 is inserted and guided into the eye 136 via manipulation of handle 114. The predetermined contracted profile of the net 112 facilitates insertion of the net into the capsule 138 and positioning of the net behind the nucleus 140 with the net in the contracted configuration. Insertion and positioning of the net 112 behind the nucleus 140 is further facilitated by the geometric or dimensional stability of the net in the contracted configuration. The predetermined contracted profile presented by arm 121 also enhances proper positioning since the arm need only be aligned approximately with the center of the nucleus 140.

Once the net 112 in the contracted configuration is properly positioned behind the nucleus 40, the actuator 126 is depressed to effect movement of net 112 from the contracted configuration to the expanded configuration as shown in FIG. 10. In the expanded configuration, net 112 substantially corresponds to the curvature of the posterior capsular wall 146, and the nucleus 140 protrudes into net 112 through entry opening 120 such that the posterior nucleus is encompassed by net 112. With the net 112 thusly deployed between the nucleus 140 and the rupture 144, the nucleus 140 remains uncaptured by the net 112 so that fragmentation and aspiration of the nucleus with a fragmenting instrument 142 separate and independent from the lenticular net instrument 110 may be safely resumed or continued since migrating nuclear fragments enter the entry opening 120 and are collected in net 112. Migrating fragments of nucleus 140 are thereby prevented from passing posteriorly into the vitreous cavity and, rather, will pass into and be collected by net 112. Once the cataractous nucleus 140 and nuclear fragments have been removed via aspiration through the fragmenting instrument 142, the net 112 is moved from the expanded configuration to the contracted configuration for removal from the eye 136. The openwork material 118 will be trapped or retained between the frame parts 116*a* and 116*b* in the contracted configuration, the contracted frame 116 assuming a narrow profile to facilitate removal. The net 112 in the contracted configuration is then withdrawn from the capsule 138 and from the eye 136 via the incision 150.

Figure 11:
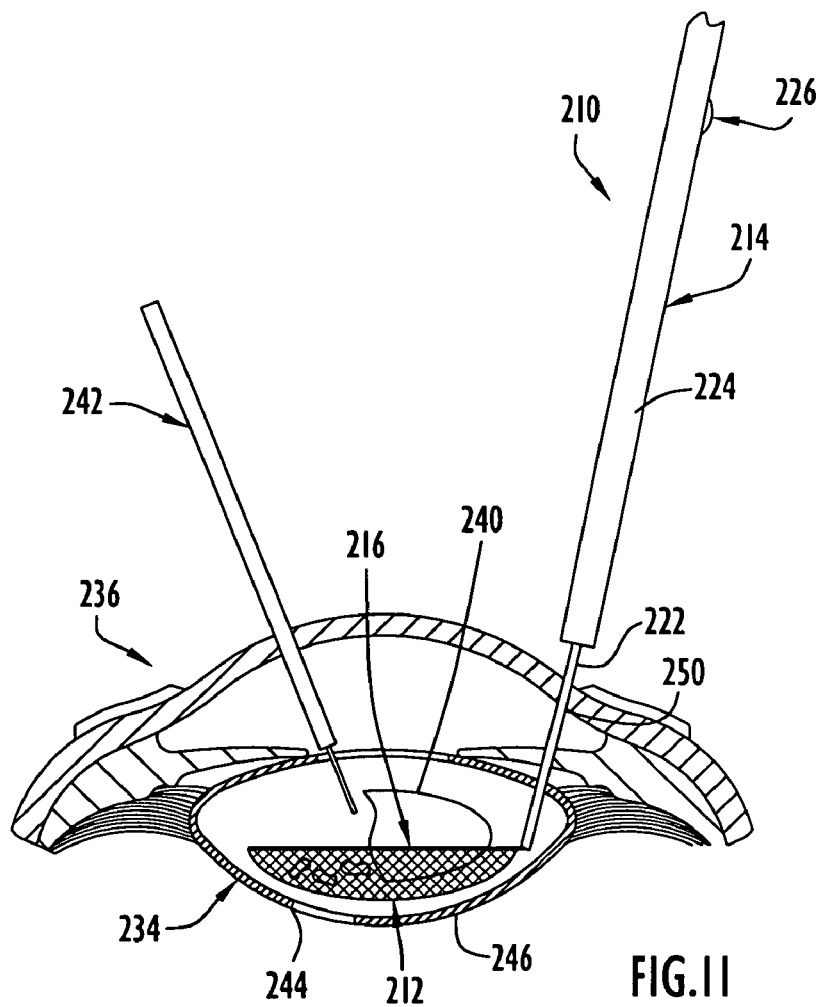
FIG. 11 is a broken view, party in section, depicting another alternative lenticular net instrument introduced in the eye through a corneal limbus incision and showing the lenticular net moved to the expanded configuration between the nucleus and a ruptured posterior capsular wall.

FIG. 11 illustrates another modified lenticular net instrument 210 used in an alternative method of cataract extraction in which the lenticular net instrument 210 is introduced in the eye 236 through a small corneal limbus paracentesis incision 250. Lenticular net instrument 210 is similar to lenticular net instrument 110 except that the handle shaft of the handle 214 for lenticular net instrument 210 does not have its distal portion disposed at an angle to its proximal portion. Rather, the distal portion 222 and the proximal portion 224 of the handle shaft for handle 214 are coaxially aligned. Also, the distal end of distal portion 222 forms an angle with the plane of frame 216 in the expanded configuration. This arrangement is different from the frame 116 and handle 114 in that the distal portion 122 of handle 114 extends in the same direction as the plane of frame 116 in the expanded configuration, as shown in FIG. 10, whereas the distal portion 222 extends at an angle to the plane of frame 216 in the expanded configuration. The method of cataract extraction depicted in FIG. 11 is similar to that discussed above, except that the lenticular net 212, in the contracted configuration, is introduced in and withdrawn from the eye 36 through the corneal limbus paracentesis incision 250. Many eye surgeons routinely form a corneal limbus paracentesis incision in the eye as part of the cataract extraction procedure, and this already formed incision can be utilized for introduction and withdrawal of the lenticular net instrument such that an additional incision does not have to be formed in the eye specifically to introduce and withdraw the lenticular net.

The lenticular nets are and remain mechanically connected to the handles during insertion, during removal and while deployed in the lens capsule to facilitate accurate, controlled guidance and positioning. Also, the handles enable the position of the nets behind the nucleus to be adjusted. Movement of the nets from the contracted configuration to the expanded configuration and back to the contracted configuration is mechanically controlled and not random. The lenticular nets may be moved automatically between the contracted and expanded configurations in response to movement of an actuator on the handles. Movement of the nets between the contracted and expanded configurations may be effected automatically as a result of the lenticular nets being retracted in and extended from the handles. The lenticular net instruments need not be used unless needed in the event of a ruptured capsular wall. The lenticular net instruments are thusly not inserted in a patient's eye unnecessarily but only when conditions warrant. Cataract surgery is thereby made safer for the patient, and the cost associated with using additional instruments or secondary procedures to retrieve nuclear fragments are avoided. The lenticular nets have a size in the expanded configuration to capture the lens nucleus or its fragments. The lenticular nets may encompass the nucleus posteriorly, and the nets may encompass the posterior nucleus entirely or partially entirely while leaving the nucleus uncaptured and, therefore, accessible for fragmentation by a fragmenting instrument separate and independent from the lenticular net instrument. The lenticular net instruments can be supplied in sterile packages which can remain unopened until just prior to insertion of the instruments in the eye such that unused instruments can be saved for use in future procedures. The lenticular net instruments can be economically designed and manufactured to be disposable for single patient use.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A lenticular net instrument for use in extracapsular cataract surgery in which a cataractous nucleus is fragmented, comprising
 a lenticular net, a handle coupled with said lenticular net and an actuator on said handle for effecting movement of said lenticular net to a contracted configuration having a narrow profile permitting insertion in and withdrawal from a lens capsule through a small incision and an expanded configuration having an expanded profile behind a cataractous nucleus to block fragments of the nucleus from falling into the vitreous cavity, said narrow profile being of a size small enough to fit through a 1 to 2 mm incision in the eye, said lenticular net comprising a layer of openwork material collapsed in the contracted configuration and expanded in the expanded configuration, said layer of openwork material having a plurality of openings therein of a size preventing clinically significant fragments of the nucleus from passing therethrough into the vitreous cavity, said lenticular net in said expanded configuration leaving the nucleus uncaptured by said net for fragmentation by a fragmenting instrument separate and independent from said lenticular net instrument.

2. The lenticular net instrument recited in claim 1 wherein said lenticular net comprises a frame carrying said layer of openwork material, said frame being collapsed in said contracted configuration and being expanded in said expanded configuration.

3. The lenticular net instrument recited in claim 2 wherein said frame comprises a pair of arms extending angularly outwardly away from one another in a distal direction in said expanded configuration and moved inwardly toward one another in said contracted configuration, said layer of openwork material extending between said arms.

4. The lenticular net instrument recited in claim 3 wherein said arms assume a V-shaped configuration in said expanded configuration.

5. The lenticular net instrument recited in claim 3 wherein said arms are biased angularly outwardly away from one another in said distal direction in said expanded configuration.

6. The lenticular net instrument recited in claim 5 wherein said arms comprise wires having a spring bias biasing said arms angularly outwardly away from one another in said distal direction in said expanded configuration.

7. The lenticular net instrument recited in claim 1 wherein said handle comprises a handgrip and an elongate tubular sleeve extending distally from said handgrip to an open distal end and further including an operating member mechanically coupling said actuator to said lenticular net, said operating member being slidably disposed in said sleeve and being movable proximally by said actuator relative to and within said sleeve to retract said lenticular net within said sleeve to obtain said contracted configuration and being movable distally by said actuator relative to and within said sleeve to extend said lenticular net distally from said open distal end of said sleeve to obtain said expanded configuration, said sleeve having a cross-sectional size permitting insertion in and withdrawal from the lens capsule through a 1 to 2 mm incision.

8. The lenticular net instrument recited in claim 7 wherein said sleeve is curved between said handgrip and said open distal end.

9. The lenticular net instrument recited in claim 8 wherein said operating member comprises a flexible shaft within said sleeve.

10. The lenticular net instrument recited in claim 9 wherein said shaft comprises one or more flexible wires.

11. The lenticular net instrument recited in claim 7 wherein said actuator includes a finger pad slidable distally and proximally along a longitudinal slot in said handgrip to move said operating member distally and proximally relative to and within said sleeve.

12. The lenticular net instrument recited in claim 1 wherein said layer of openwork material comprises a layer of biocompatible plastic having said openings therein.

13. The lenticular net instrument recited in claim 1 wherein said layer of openwork material folds in said contracted configuration and unfolds in said expanded configuration.

14. The lenticular net instrument recited in claim 1 wherein said layer of openwork material is made of a non-phacoemulsifiable material.

15. The lenticular net instrument recited in claim 1 wherein said net in said contracted configuration assumes the shape of a singular narrow arm.

16. The lenticular net instrument recited in claim 15 wherein said singular narrow arm is disposed in a plane.

17. The lenticular net instrument recited in claim 16 wherein said arm is curved within said plane.

18. The lenticular net instrument recited in claim 1 wherein said layer of openwork material has a curvature in said expanded configuration corresponding to the anatomical curvature of the posterior wall of the lens capsule.

19. The lenticular net instrument recited in claim 1 wherein said net in said expanded configuration is adapted to avoid creating traction on the vitreous gel.

* * * * *